US006660493B2

(12) United States Patent
Miles

(10) Patent No.: US 6,660,493 B2
(45) Date of Patent: Dec. 9, 2003

(54) HYDRODYNAMIC ENHANCED DIELECTROPHORETIC PARTICLE TRAPPING

(75) Inventor: Robin R. Miles, Danville, CA (US)

(73) Assignee: The Regents of the University of California, Oakland, CA (US)

(*) Notice: Subject to any disclaimer, the term of this patent is extended or adjusted under 35 U.S.C. 154(b) by 441 days.

(21) Appl. No.: 09/819,410

(22) Filed: Mar. 28, 2001

(65) Prior Publication Data

US 2003/0152920 A1 Aug. 14, 2003

(51) Int. Cl.[7] .......................... C12Q 1/24; G01N 27/26

(52) U.S. Cl. .................. 435/30; 435/173.9; 435/287.3; 204/547; 204/643

(58) Field of Search ............................... 435/30, 287.3, 435/173.9; 204/547, 643

(56) References Cited

PUBLICATIONS

Becker et al., PNAS, vol. 92, 1995, pp. 860–864.*

* cited by examiner

*Primary Examiner*—James Ketter
(74) *Attorney, Agent, or Firm*—Eddie E. Scott; L. E. Carnahan; Alan H. Thompson

(57) ABSTRACT

Hydrodynamic enhanced dielectrophoretic particle trapping carried out by introducing a side stream into the main stream to squeeze the fluid containing particles close to the electrodes producing the dielelectrophoretic forces. The region of most effective or the strongest forces in the manipulating fields of the electrodes producing the dielectrophoretic forces is close to the electrodes, within 100 $\mu$m from the electrodes. The particle trapping arrangement uses a series of electrodes with an AC field placed between pairs of electrodes, which causes trapping of particles along the edges of the electrodes. By forcing an incoming flow stream containing cells and DNA, for example, close to the electrodes using another flow stream improves the efficiency of the DNA trapping.

16 Claims, 2 Drawing Sheets

HYDRODYNAMIC ENHANCED DIELECTROPHORETIC PARTICLE TRAPPING

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to particle trapping, particularly to trapping of DNA and cells/spores using dielectrophoretic forces, and more particularly to hydrodynamic enhanced dielectrophoretic particle trapping by introducing a side stream of fluid into the main stream of fluid containing particles for forcing the particles closer to electrodes producing the dielectrophoretic forces.

Trapping of DNA and cells/spores using dielectrophoretic (DEP) forces is being considered for performing sample preparation protocols for polymerized chain reaction (PCR) based assays for counter biological warfare applications, as well as for a clinical tool to determine genetic information and other medical applications. A key element of the sample preparation process is to enable controlled concentration and/or movement of DNA, for example, prior to detection. DEP forces are strongest near the electrodes which create manipulating fields. The region of effective force is less than 100 μm from the electrodes. Small channels manufactured to bring the fluid containing the particles close to the electrodes have been considered, but this enhances the probability of clogging the small channels, since biological materials are very sticky and plug channels easily.

The present invention solves the problem by introducing a side stream into the main stream to force or squeeze the fluid containing particles close to the electrodes such that the particles would be affected by the DEP forces, but would allow for a relatively open or larger channel to prevent clogging. The invention utilizes a series of electrodes located along a length of an electrophoretic channel. Since DEP forces induce a dipole in the sample particles, these particles can be trapped in non-uniform fields located along the channel, and which are produced by the electrodes. Thus, the present invention provides for hydrodynamic enhanced dielectrophoretic particle trapping.

SUMMARY OF THE INVENTION

It is an object of the present invention to provide enhanced particle trapping using dielectrophoretic forces.

A further object of the invention is to provide hydrodynamic enhanced dielectrophoretic particle trapping.

Another object of the invention is to provide enhanced dielectrophoretic particle trapping by forcing the particle containing fluid close to electrodes which produce the dielectrophoretic forces.

Another object of the invention is to provide hydrodynamic enhanced dielectrophoretic particle trappings by introducing a side stream into the main particle containing stream to squeeze the main stream close to electrodes which produce dielectrophoretic forces such that the particles are affected by the dielectrophoretic forces thereby enhancing particle trapping.

Other objects and advantages of the present invention will become apparent from the following description and accompanying drawings. Basically, the present invention provides for trapping of particles using dielectrophoretic (DEP) forces. More specifically the invention involves a method and apparatus for hydrodynamic enhanced DEP particle trapping. This is accomplished by the use of side stream flows to direct main stream flows. Since DEP forces are effective only very close to the electrodes (less than 100 μm), it is important to direct the cells and DNA close to the electrodes. This is accomplished by the invention by using side stream flows. Use of side stream flows in lieu of making smaller channels reduces the chance of blockage of the flow channels, which is very common in biosystems. The apparatus of the invention includes a series of electrodes, which may be photolithographically patterned along the side of a sample flow or fluidic channel, with an AC field placed between pairs of electrodes. The AC field induces a dipole in the DNA or cell or spore which at certain frequencies, traps the particles along the edges of the electrodes. The sample or incoming flow stream containing the cells and DNA is forced close to the electrodes using a side stream flow, which improves the efficiency of DEP trapping.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to trapping of DNA and cells/spores using dielectrophoretic (DEP) forces to perform sample preparation protocols for PCR based assays, for applications such as counter biological warfare, determining genetic information, etc. A key element for PCR sample preparation is the use of DEP forces to concentrate the DNA prior to detection. DEP forces are strongest near the electrodes. By introducing a side stream into the main stream containing the particles, the main stream is squeezed such that the particles are forced toward the electrodes and are thus more affected by the DEP forces. This invention enables the use of relatively open channels thereby preventing clogging which results from the use of small channels.

Figure 1:
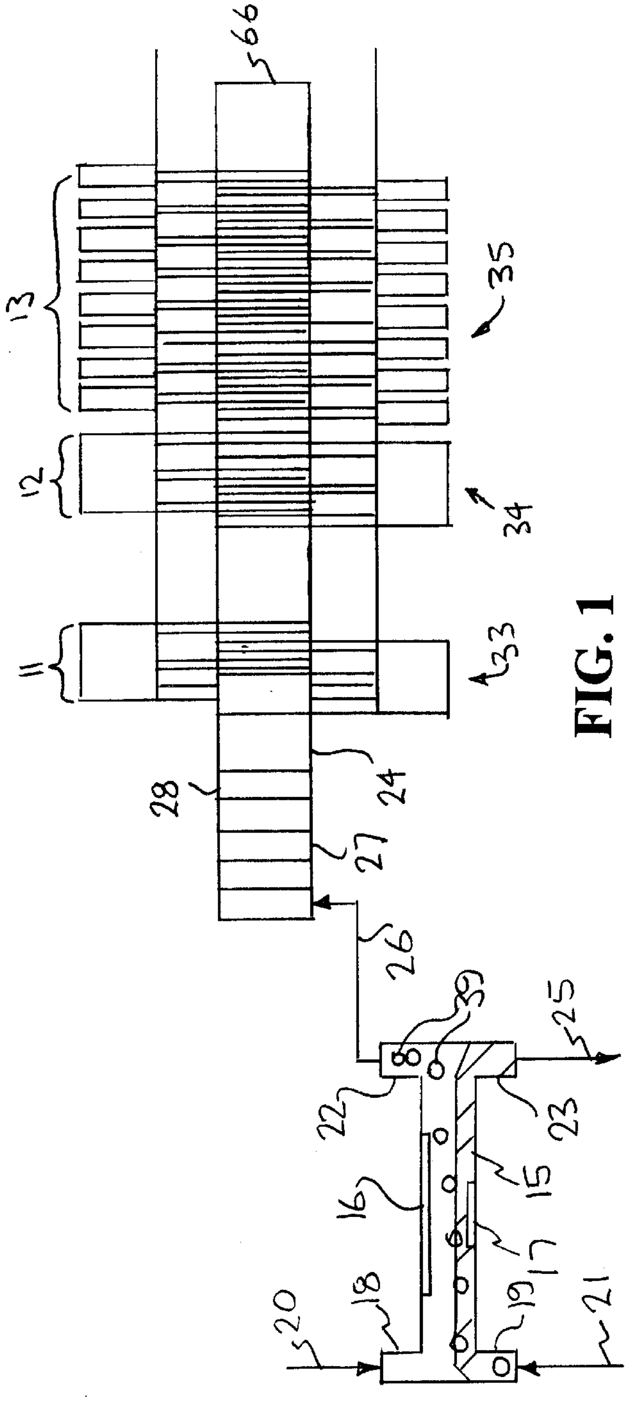
FIG. 1 is a top diagrammatic view of an embodiment of a sample preparation/assay system utilizing hydrodynamic enhance dielectrophoretic particle trapping in accordance with the present invention.
Figure 2:
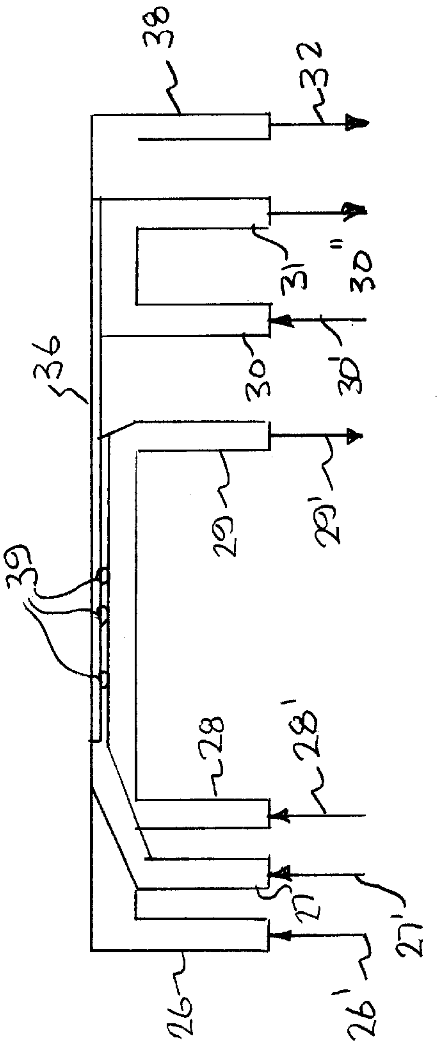
FIG. 2 is a side view of a portion of the FIG. 1 system.

FIGS. 1 and 2 schematically illustrate a PCR sample preparation system which incorporates the hydrodynamic enhanced DEP particle trapping of the present invention, as exemplified in FIGS. 3 and 4 and described in detail hereinafter. FIG. 1 is a top view of the overall system and FIG. 2 is a side view of a portion of the FIG. 1 system. As shown, the system incorporates four (4) sections or functions which include sample fractionation indicated at 10, sample concentration indicated 11, DNA concentration indicated at 12, and DNA motion/reagent mix indicated at 13. The sample fractionation section 10 includes a flow channel 15 in which electrodes 16–17 for DEP are mounted, with channel 15 having inputs or inlets 18 and 19 into which are directed a focusing buffer 20 and a sample 21 (from an aerosol collector, for example) and outlets 22 and 23, connected to a channel 24 and to waste 25.

Channel 24 extends though section 11–13 of the system and includes 3 inlets, a sample inlet 26, a lysing solution inlet 27, and a focusing buffer inlet 28, see FIG. 2, for sample 26', lysing solution 27' and focusing buffer 28' and is provide with a waste outlet 29, a PCR reagent inlet 30 and outlet 31, and exit 32, for waste 29' and reagent 30' and 30". The channel 24 is also provided with electrode sets indicated at 33 for section 11, 34 for section 12 and 35 for section 13 and with a single electrode 36, see FIG. 2, which extends the length of electrode sets 33, 34, and 35. The electrode sets 33–35 and single electrode 36 are electrically connected to an AC power source 37 as in FIG. 3. The channel 24 terminates via a detector which includes ports 38. As charged particles, such as DNA, 39 from outlet 22 of channel 15 of sample fractionation section 10 pass along channel 24 the electrodes of electrode sets 33, 34, and 36 are each sequentially activated to control the concentration of the particles via electrical fields produced by the sequentially activated electrodes. As seen in FIGS. 1 and 2 a sample 26' containing particles 39 is introduced into flow channel 24, wherein the particles (cells and spores) are captured on the electrodes of electrode set 33 by DEP forces. As seen in FIG. 2, a focusing buffer 28 via inlet 28 and a lysing solution 27' are introduced into channel 24, the lysing solution 27' breaking open the spores to release the DNA and the focusing buffer 28' squeezing sample toward the electrodes 62. The DNA travels downstream to another set 34 of electrodes where the DNA is captured. The DNA is walked down the channel 24 to a low-flow area, section 13, via electrode set 35, where PCR reagents 30 are introduced. The sample is then released for the PCR process and detection.

A key factor to the success of the system of FIGS. 1–2 is that flows in small dimensional (<500 $\mu$m) channels is laminar. Mixing between streams is limited to diffusion, which is not very effective. Thus, side stream flows can be used to direct other flows. Since DEP forces are effective only very close (<100 $\mu$m) to the electrodes, it is important to direct the cells and DNA close to the electrodes. This can be accomplished using side stream flows, as shown at in FIGS. 1–2 at inlet 28 and the focusing buffer flow indicated at 40, and illustrated in greater detail in FIGS. 3–4 described hereinafter. Use of side stream flows in lieu of making smaller channels reduces the chance of blockage of the flow channels, which is very common in biosystems.

Figure 3:
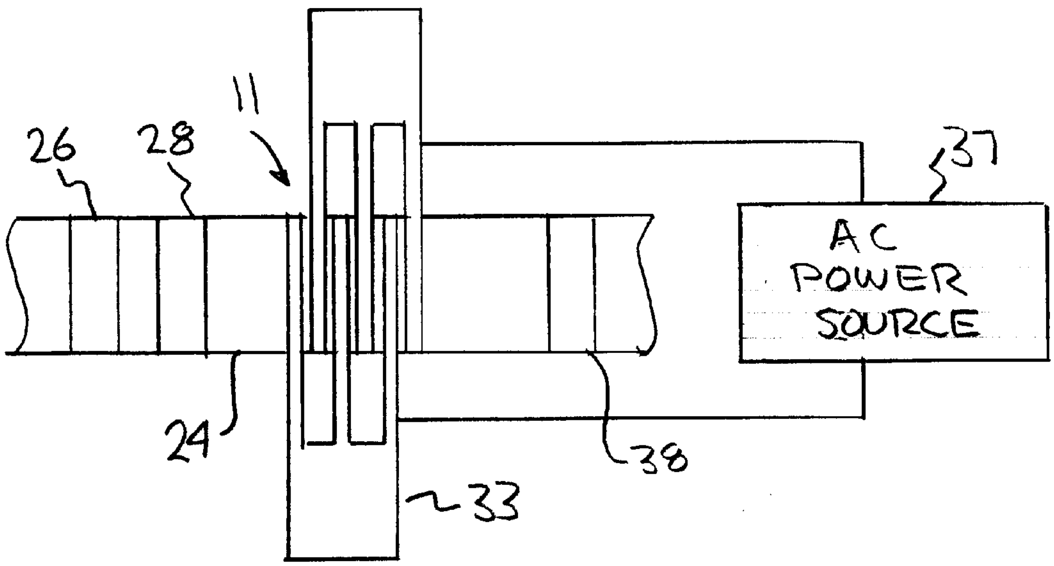
FIG. 3 is a top view of a fluidic channel in which is located to DEP electrodes and a hydrodynamic (side stream) for carrying out the invention.
Figure 4:
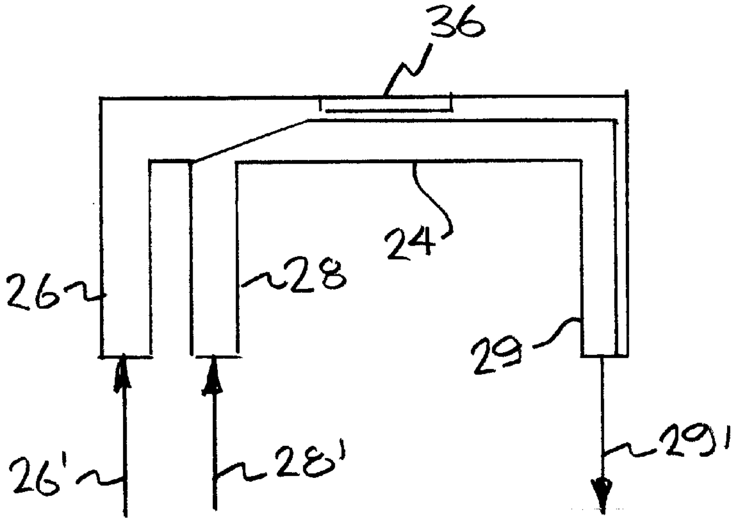
FIG. 4 is a partial side view of the FIG. 3 device illustrating the main (sample) flow stream and the side (hydrodynamic) flow stream.

FIGS. 3 and 4 illustrate a simplified embodiment of the hydrodynamic enhanced DFP particle trapping of the FIGS. 1–2 system, and corresponding components are given corresponding reference numerals. As clearly seen in FIG. 4, the sample fluid with particles 26' passing via inlet 26 and channel 24 is squeezed close to electrode 36 by the side stream or focusing fluid 28' via inlet 28, whereby the particles in sample fluid 26' are affected by the DEP forces and trapped along electrode 36 as indicated at 39 in FIG. 2.

It has thus been shown that the present invention enables hydrodynamic enhanced dielectrophoretic particle trapping and enables movement and concentration of particles in a fluidic channel via DEP forces through sequentially activated electrodes, which produce trapping via electric fields. The invention solves the problem of directing the particles close to the electrodes for increase DEP force affect thereon without the use of small channels, thereby reducing potential clogging of the channels while increasing the efficacy of DEP trapping. The invention is particularly applicable for use in counter biological warfare as well as a clinical tool to determine genetic information via PCR processing.

While particular embodiments of the invention have been described and illustrated to exemplify and teach the principles of the invention, such are not intended to be limiting. Modifications and changes may become apparent to those skilled in the art and it is intended that the invention be limited only by to scope of the appended claims.

What is claimed is:

1. In a sample preparation system using a fluidic channel and dielectrophoretic forces, the improvement comprising:

hydrodynamic enhanced dielectrophoretic particle trapping.

2. The improvement of claim 1, wherein the hydrodynamic enhanced particle trapping is carried by squeezing a particle carrying fluid adjacent electrodes creating the dielectrophoretic force.

3. The improvement of claim 2, wherein squeezing the particle carrying fluid is carried out by introducing a side stream fluid into the particle carrying fluid.

4. The improvement of claim 2, wherein squeezing the particle carrying fluid is carried out by providing the fluidic channel with an inlet located downstream from an inlet for the particle carrying fluid, and introducing through the downstream inlet a side stream fluid.

5. In a system having at least one fluidic channel through which particle containing fluid is adapted to flow and having at least one pair of electrodes located adjacent surfaces of the fluidic channel for producing dielectrophoretic forces, the improvement comprising:

means for forcing the particle containing fluid close to the electrodes.

6. The system of claim 5, wherein said means includes a side stream fluid directed against the particle containing fluid.

7. The system of claim 6, wherein said fluidic channel includes an inlet for the particle containing fluid, and wherein said means additionally includes an inlet in said fluidic channel located downstream from the inlet for the particle containing fluid, the side stream fluid being directed through the downstream inlet and against the particle containing fluid.

8. A system for hydrodynamic enhanced dielectrophoretic trapping, comprising:

a sample preparation apparatus having at least one fluid channel, at least one pair of spaced electrodes being located along a length of said at least one fluid channel, means for producing an electric field between said at least one pair of spaced electrodes, said at least one fluid channel having at least a pair of fluid inlets, one of said pair of fluid inlets being located downstream and in spaced relation to another of said pair of fluid inlets, and a side stream fluid adapted to be directed through said downstream fluid inlet and against an associated particle carrying fluid adapted to pass through said fluid channel such that such an associated particle carrying fluid is squeezed toward said pair of spaced electrodes, whereby particles in such an associated particle carrying fluid are trapped against one of said pair of electrodes.

9. The system of claim 8, wherein a plurality of pairs of electrodes are located along a length of said at least one fluid channel.

10. The system of claim 9, wherein said plurality of pairs of electrodes are of an interdigitated construction.

11. The system of claim 9, wherein said plurality of pairs of electrodes are constructed such that each pair of electrodes have a common electrode.

12. The system of claim 8, wherein said at least one pair of spaced electrodes are located on different surfaces of said at least one fluid channel.

13. The system of claim 8, wherein said side stream fluid is composed of a focusing buffer fluid.

14. The system of claim 8, additionally including a third fluid inlet for directing a lysing solution into said at least one fluid channel.

15. The system of claim 14, wherein said third fluid inlet is located intermediate said pair of fluid inlets.

16. The system of claim 8, additionally including means for introducing a PCR reagent into said at least one fluid channel, said means being located downstream from a point of introduction of said side stream fluid into said at least one fluid channel.

* * * * *